United States Patent [19]

Byrum

[11] Plant 4,631

[45] Jan. 27, 1981

[54] SEEDLING ROSE PLANT

[75] Inventor: Roy L. Byrum, Richmond, Ind.

[73] Assignee: Joseph H. Hill Company, Richmond, Ind.

[21] Appl. No.: 66,868

[22] Filed: Aug. 15, 1979

[51] Int. Cl.[3] ..... A01H 5/00

[52] U.S. Cl. ..... Plt./11

[58] Field of Search ..... Plt./11

*Primary Examiner*—Robert E. Bagwill

*Attorney, Agent, or Firm*—Chas. W. Rummler

[57] ABSTRACT

A new and distinct bi-colored rose plant for greenhouse culture and cut flower production, distinguished by the Talisman coloration of its medium sized blooms which is intense and brilliant both in the bud stage and as an open flower, and by its above average vase life and keeping qualities as a cut flower. This rose plant has a vigorous growth habit with a continuous and abundant production of flowers, borne singly on stems of medium length, and an abundance of dark green, glossy foliage.

1 Drawing Figure

BACKGROUND OF THE NEW PLANT

This new rose plant originated as a seedling resulting from a cross of Cotillion (U.S. Plant Pat. No. 2,978) by Hoosier Gold (U.S. Plant Pat. No. 3,544) made at Richmond, Ind., in March 1973, with the object of producing a more vivid bi-colored flower than its seed parent while maintaining the vigorous growth of the pollen parent and the disease resistant characteristic of both parents. This rose was discovered by me in October 1974 and was reproduced by me, by budding, at Richmond, Ind., to determine and test its true characteristics, and propagation in a like manner through successive generations has demonstrated that the objectives of the original crossing have been accomplished and appear to be firmly fixed, holding true from generation to generation.

This plant is now being commercially propagated, by budding, at Hamilton City, Calif.

DESCRIPTION OF THE DRAWING

My new variety of rose plant is illustrated by the accompanying full color photographic drawing which shows several stages of its buds, a newly opened flower, and a full face view of a fully opened, three day bloom. The drawing also shows specimens of young wood and typical leaves of the blooming plant. At the bottom left of the drawing, the outside (top row) and inside surfaces of the outside, intermediate, and inner petals of a newly opened flower are shown, and similarly, at the bottom right of the drawing, the outside (bottom row) and inside petal surfaces of a three-day opened bloom are shown. The colors shown are as nearly true as can be reasonably expected to be reproduced by conventional photographic procedures.

DESCRIPTION OF THE NEW PLANT

The following is a detailed description of my new variety of rose plant based upon observations of greenhouse plants grown at Richmond, Ind., and made in the month of February 1979, the color designations being according to the Robert S. Wilson Horticultural Colour Chart (W) and Koster's Colour Guide (K).

THE PLANT

Origin: Seedling.

Parentage:

*Seed parent.*—Cotillion (U.S. Plant Pat. No. 2,978).

*Pollen parent.*—Hoosier Gold (U.S. Plant Pat. No. 3,544).

Classification: Hybrida.

Type: Greenhouse plant for cut flower production.

Form: Bush.

Growth: Free and vigorous.

Habit: Upright and much branched.

Canes: Medium in diameter.

Main stems: Color — nearest, Sage Green 00861 (W) overlaid with very light shading of Violet Plate No. 59 (K).

*Thorns.*—Several; straight and with short, broad base. Color: Violet Plate No. 59 (K).

*Prickles.*—Several in number. Color: Violet Plate No. 59 (K).

Branches: Color — Scheeles Green 860 (W).

*Thorns.*—Many, of medium length and hooked downward from a long, narrow base. Color: Brick Red 016/3 (W).

*Prickles and hairs.*—None.

New shoots: Color — Lettuce Green 861/3 (W).

*Thorns.*—Many, of medium length and hooked downward from a long, narrow base. Color: Lilac Rose Plate No. 49 (K).

*Prickles and hairs.*—None.

Foliage:

*Quantity.*—Abundant.

*Leaves.*—Compound and odd pinnate. Size: Medium large.

*Leaflets.*—Number — 5 or 7. Shape: Ovoid with round base, acute apex, and serrate margin. Aspect: Heavy. Color: Young leaves: Upper surface — Lettuce Green 861/3 (W) overlaid with deep Carmine Violet Plate No. 46 (K). Under surface — Lettuce Green 861/3 (W) overlaid with deep Carmine Violet Plate No. 46 (K). Mature leaves: Upper surface — nearest color, Spinach Green 0960 (W). Under surface — nearest color, Cedar Green Plate No. 80 (K).

*Rachis.*—Medium heavy in size. Upper side: Smooth. Under side: Moderately prickly.

*Stipules.*—Narrow and of medium length with short points turning out at an angle of less than 45° from the stem.

THE BUD

Before calyx breaks:

*Size.*—Medium small.

*Form.*—Short pointed with a conspicuous neck and with foliaceous appendages on the surface of the bud with much cut parts extending beyond the tip of the bud a distance equal to three-quarters or more of the bud length.

*Color.*—Scheeles Green 860 (W).

As the calyx breaks:

*Color (outside of the petal).*—Indian Yellow 6/2 (W).

As the first petal opens:

*Bud size.*—Small.

*Form.*—Short pointed.

*Color of petal.*—Outside — Indian Yellow 6 (W). Inside — Indian Orange 713/1 (W) with Indian Yellow 6/1 (W) at the base.

Character of opening: The bud opens up well in greenhouse.

Sepals: Permanent.

*Shape.*—Spear-shaped and moderately long and curled.

*Color.*—Inside — Scheeles Green 860/2 (W) overlaid with white fuzz. Outside — Scheeles Green 860/1 (W) with white fuzz showing around edge.

Peduncle:

*Size.*—Strong and erect, of medium diameter and medium length.

*Bark.*—Peduncle is entirely smooth. Color: Scheeles Green 860/1 (W).

*Thorns, prickles and hairs.*—None.

THE FLOWER

Blooming habit: Abundant and continuous in greenhouse.

Size: Medium small when fully opened — 2 to 3 inches in diameter.

Form: High centered at first with petals tightly rolled outward, becoming open as the bloom matures with the petals loosely rolled outward.

Borne: Singly on medium strong stems of medium length.

Petalage: Double with 20 to 25 petals arranged regularly.

*Shape.*—Outside and intermediate petals — obovate with cuspidate apex. Inside petals — spatulate, most with 2 or 3 notches.

*Texture.*—Moderately thick.

*Appearance.*—Inside surface — shiny. Outside surface — satiny.

Color:

A. The following is the color description of a newly opened greenhouse rose observed in the month of June 1980:

*Outside petals.*—Outer surface — the base is Indian Yellow 6/2 (W) gradually changing to 6/3 (W) toward the top. Also, very lightly tinted with Brick Red 016/1 (W) at the top of the petal. Inside surface — the base is Indian Yellow 6/1 (W) changing to Brick Red 016 (W).

*Intermediate petals.*—Outer surface — the base is Indian Yellow 6/2 (W) gradually changing to 6/3 (W) toward the top of the petal, which is margined with Brick Red 016/1 (W). Inside surface — the base is Indian Yellow 6/1 (W) changing to Brick Red 016/1 (W).

*Inner petals.*—Outside surface — the base is Indian Yellow 6/2 (W) changing to 6/3(W) toward the top with a light margin of Brick Red 016/1 (W). Inside surface — the base is Indian Yellow 6/1 (W) changing to Brick Red 016/1 (W).

B. This description was made from observations of a rose that was opened for three days in greenhouse in the month of June 1980:

*Outside petals.*—Outer surface — Indian Yellow 6/1 (W) at the base gradually changing to 6/2 (W) toward the top and slightly tinted with Brick Red 016/2 (W) at the tip. Inside surface — Indian Yellow 6/1 (W) at the base gradually changing to Brick Red 016/1 (W) at the top.

*Intermediate petals.*—Outside surfaces — Indian Yellow 6/1 (W) at the base gradually changing to Brick Red 016/1 (W) toward the top. Inside surfaces — Indian Yellow 6/1 (W) at the base gradually changing to Brick Red 016/1 (W).

*Inner petals.*—Outside surface — Indian Yellow 6/1 (W) at the base gradually changing to Indian Yellow 6/2 (W) at the top. Inside surface — Indian Yellow 6/1 (W) at the base gradually changing to Brick Red 016/1 (W).

General color effect of open bloom:

*Newly opened flower.*—Predominantly Brick Red 016 (W).

*Three days opened bloom.*—The predominant coloration is Brick Red 016/1 (W).

Persistence: The petals hang on and dry.

Lasting quality: Five to seven days in February for cut roses grown in greenhouse and kept at living room temperatures.

REPRODUCTIVE ORGANS

Stamens: Many in number and regularly arranged about the pistils.

*Filaments.*—Some are short and some are of medium length, most with anthers. Color: Indian Yellow 6/3 (W).

*Anthers.*—Medium in size and all open at once. Color: Indian Yellow 6/2 (W) with outside edge Indian Yellow 6 (W).

*Pollen.*—Abundant in quantity. Color: Straw Yellow 604/2 (W).

Pistils: Medium in number.

*Styles.*—Of medium length and very uneven, thin in size and bunched. Color: Empire Yellow 603/3 (W).

*Stigmas.*—Color — Creamy White Plate 2 (K).

Ovaries: No hips observed.

Seeds: None.

The most distinctive and novel feature of this seedling rose is the intense and brilliant bi-color of the bloom both in the bud stage and as an open flower. This seedling also distinguishes itself further by exhibiting very good vase life and keeping qualities as a cut flower.

This new plant is considered to be a material improvement over its seed parent, Cotillion, in that the flower color is more vivid and brilliant and the abundance of dark green, glossy foliage further accentuates and enhances the brilliance of the flower color. Also, the growing habits of this plant are more responsive and vigorous than those of the seed parent even under the poor light conditions of winter months.

With respect to the pollen parent, Hoosier Gold, this new plant has been found to have better bud formation and longer stems as a cut flower. Also, this new seedling would be classed categorically as of Talisman coloration, whereas Hoosier Gold is a solid yellow color flower.

I claim:

1. A new and distinct variety of rose plant substantially as herein shown and described, characterized by its abundant and continuous production of medium sized flowers of Talisman coloration borne on medium strong stems of medium length, and by its vigorous and responsive growth habits under the poor light conditions of winter months.

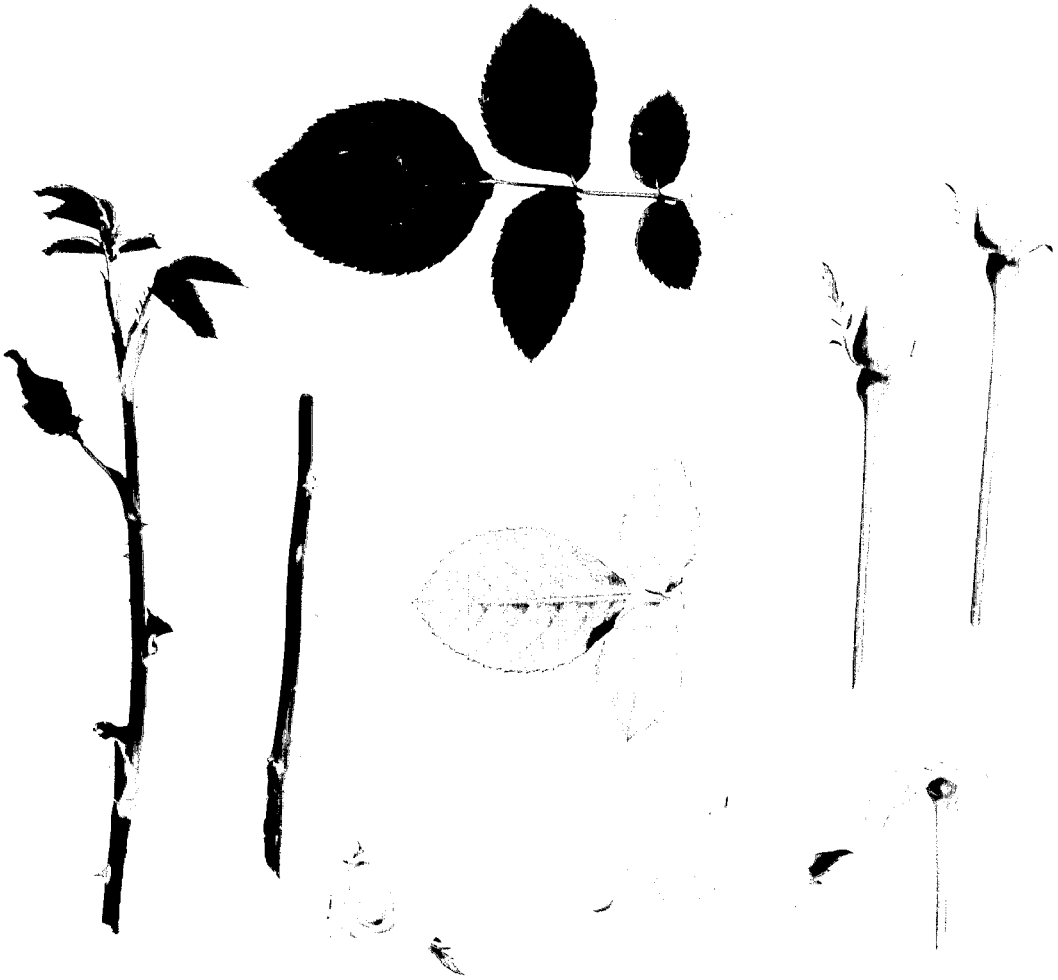

* * * * *